(12) United States Patent
Bareket et al.

(10) Patent No.: US 11,896,526 B2
(45) Date of Patent: Feb. 13, 2024

(54) LASER BEAM CALIBRATION AND BEAM QUALITY MEASUREMENT IN LASER SURGERY SYSTEMS

(71) Applicant: AMO DEVELOPMENT, LLC, Irvine, CA (US)

(72) Inventors: Noah Bareket, Saratoga, CA (US); David A. Dewey, Sunnyvale, CA (US); Michael J. Simoneau, Morgan Hill, CA (US)

(73) Assignee: AMO Development, LLC, Irvine, CA (US)

( * ) Notice: Subject to any disclaimer, the term of this patent is extended or adjusted under 35 U.S.C. 154(b) by 775 days.

(21) Appl. No.: 16/885,252

(22) Filed: May 27, 2020

(65) Prior Publication Data

US 2020/0289317 A1  Sep. 17, 2020

Related U.S. Application Data

(62) Division of application No. 15/299,745, filed on Oct. 21, 2016, now Pat. No. 10,667,949.

(Continued)

(51) Int. Cl.
*A61F 9/08* (2006.01)
*A61F 9/008* (2006.01)
*A61F 9/009* (2006.01)

(52) U.S. Cl.
CPC .............. *A61F 9/008* (2013.01); *A61F 9/009* (2013.01); *A61F 2009/00844* (2013.01); *A61F 2009/00855* (2013.01)

(58) Field of Classification Search
CPC ....................... A61F 9/008; A61F 9/009; A61F 2009/00844; A61F 2009/0085

(Continued)

(56) References Cited

U.S. PATENT DOCUMENTS

| 5,261,822 A | 11/1993 | Hall et al. |
| 5,460,627 A | 10/1995 | O'Donnell, Jr. |

(Continued)

FOREIGN PATENT DOCUMENTS

| CN | 104010602 A | 8/2014 |
| DE | 102006007751 A1 | 8/2007 |

(Continued)

OTHER PUBLICATIONS

Gao X., et al., "Beam-Shaping Technique for Improving the Beam Quality of a High-Power Laser-Diode Stack," Journal of Optics Letters, 2006, vol. 31 (11), pp. 1654-1656.

(Continued)

*Primary Examiner* — Shirley X Jian
(74) *Attorney, Agent, or Firm* — Johnson & Johnson Surgical Vision, Inc.

(57) ABSTRACT

A laser eye surgery system includes a computer which scans a focused laser beam in a trajectory over a reticle or target and determines beam quality via laser light reflected from the target. The target may have a grid pattern of lines, with the diameter of the focused laser beam determined based on a time interval for the scanned beam to move onto a line of the grid pattern. Methods for measuring beam quality in a laser eye surgery system provide a direct, quantitative quality measurement of the focused laser beam, and may be performed quickly and automatically. Using scanning mirror position information together with signals resulting from laser light reflected from the target, the laser eye surgery system may also be calibrated.

11 Claims, 2 Drawing Sheets

Related U.S. Application Data

(60) Provisional application No. 62/244,507, filed on Oct. 21, 2015.

(58) Field of Classification Search
USPC .................................................. 606/4
See application file for complete search history.

(56) References Cited

U.S. PATENT DOCUMENTS

| | | | |
|---|---|---|---|
| 5,464,960 A | 11/1995 | Hall et al. | |
| 5,713,893 A | 2/1998 | O'Donnell, Jr. | |
| 5,720,894 A | 2/1998 | Neev et al. | |
| 5,772,656 A | 6/1998 | Klopotek | |
| 5,841,465 A * | 11/1998 | Fukunaga | G02B 26/128 347/258 |
| 5,957,915 A | 9/1999 | Trost | |
| 5,984,916 A | 11/1999 | Lai | |
| 6,019,472 A | 2/2000 | Koester et al. | |
| 6,195,164 B1 | 2/2001 | Thompson et al. | |
| 6,210,401 B1 * | 4/2001 | Lai | B23K 26/032 606/4 |
| 6,325,792 B1 * | 12/2001 | Swinger | A61F 9/00834 606/4 |
| 6,369,898 B1 | 4/2002 | Van Saarloos et al. | |
| 6,454,761 B1 | 9/2002 | Freedman | |
| 6,585,723 B1 * | 7/2003 | Sumiya | A61F 9/00804 606/5 |
| 6,646,728 B1 * | 11/2003 | Tang | B23K 26/705 356/123 |
| 6,666,855 B2 * | 12/2003 | Somani | A61F 9/00814 250/252.1 |
| 6,678,061 B2 * | 1/2004 | Kilthau | B23K 26/04 356/243.1 |
| 6,932,806 B2 | 8/2005 | Nakamura | |
| 7,001,375 B2 * | 2/2006 | Yee | B23K 26/705 606/4 |
| 7,001,376 B2 * | 2/2006 | Somani | G01B 11/002 250/252.1 |
| 7,039,452 B2 * | 5/2006 | McClane | A61B 3/1225 600/478 |
| 7,082,151 B2 | 7/2006 | Momiuchi et al. | |
| 7,238,177 B2 * | 7/2007 | Somani | A61F 9/00802 606/4 |
| 7,456,949 B2 * | 11/2008 | Somani | A61F 9/00802 250/252.1 |
| 7,538,872 B1 | 5/2009 | Butler et al. | |
| 7,584,756 B2 | 9/2009 | Zadoyan et al. | |
| 7,612,876 B2 | 11/2009 | Widen | |
| 7,652,761 B2 * | 1/2010 | Somani | B23K 26/705 250/252.1 |
| 7,655,002 B2 | 2/2010 | Myers et al. | |
| 7,717,907 B2 | 5/2010 | Ruiz et al. | |
| 7,811,280 B2 | 10/2010 | Zickler | |
| 7,846,152 B2 | 12/2010 | Chernyak et al. | |
| 8,068,220 B2 | 11/2011 | Woittennek et al. | |
| 8,262,646 B2 | 9/2012 | Frey et al. | |
| 8,350,183 B2 | 1/2013 | Vogel et al. | |
| 8,382,745 B2 | 2/2013 | Naranjo-Tackman et al. | |
| 8,385,618 B2 | 2/2013 | Youssefi et al. | |
| 8,414,564 B2 | 4/2013 | Goldshleger et al. | |
| 8,687,178 B2 | 4/2014 | Deisinger et al. | |
| 8,764,737 B2 * | 7/2014 | Kurtz | A61F 9/00825 606/4 |
| 8,968,279 B2 * | 3/2015 | Arnoldussen | A61F 9/008 606/4 |
| 10,667,949 B2 * | 6/2020 | Bareket | A61F 9/008 |
| 10,695,220 B2 * | 6/2020 | Hertzberg | A61F 9/00825 |
| 2002/0198515 A1 * | 12/2002 | Somani | A61F 9/008 606/4 |
| 2005/0215986 A1 * | 9/2005 | Chernyak | B23K 26/705 356/10 |
| 2007/0173792 A1 * | 7/2007 | Arnoldussen | A61F 9/00804 606/4 |
| 2007/0173796 A1 | 7/2007 | Kessler et al. | |
| 2008/0165414 A1 | 7/2008 | Gray | |
| 2008/0198371 A1 | 8/2008 | Widen | |
| 2008/0221559 A1 | 9/2008 | Nguyen et al. | |
| 2011/0267446 A1 | 11/2011 | Chernyak et al. | |
| 2011/0319873 A1 | 12/2011 | Raksi et al. | |
| 2011/0319875 A1 | 12/2011 | Loesel et al. | |
| 2014/0027421 A1 | 1/2014 | Notheis | |
| 2014/0128853 A1 | 5/2014 | Angeley et al. | |
| 2014/0316389 A1 | 10/2014 | Schuele et al. | |
| 2015/0272782 A1 | 10/2015 | Schuele et al. | |
| 2015/0282988 A1 | 10/2015 | Simoneau et al. | |
| 2017/0291256 A1 * | 10/2017 | Dulaney | F41H 5/00 |
| 2019/0070788 A1 * | 3/2019 | Roesgen | B33Y 10/00 |
| 2019/0077086 A1 * | 3/2019 | Stengel | B22F 10/28 |

FOREIGN PATENT DOCUMENTS

| | | |
|---|---|---|
| DE | 102009006306 A1 | 7/2010 |
| EP | 1273279 A2 | 1/2003 |
| EP | 1273279 A3 | 12/2003 |
| JP | S5646433 A | 4/1981 |
| WO | 0120277 A1 | 3/2001 |
| WO | 02103307 A1 | 12/2002 |
| WO | 2006009916 A1 | 1/2006 |
| WO | 2009019006 A2 | 2/2009 |
| WO | 2009019006 A3 | 4/2009 |
| WO | 2012170966 A1 | 12/2012 |

OTHER PUBLICATIONS

Kokodiy N.G., et al., "Algorithms for Signal Processing of Grid Receiver for Laser Radiation," Proceedings of CAOL, 4th International Conference on Advanced Optoelectronics and Lasers 4671903, 2008, pp. 325-327.

Kokody N.G, et al., "Mathematical Modeling of Devices for Measuring of Laser Radiation Characteristics by Wire Grids (Conference paper)," Proceedings of LFNM, 6th International Conference on Laser and Fiber-Optical Networks Modeling, 2004, pp. 140-142.

Li S., et al., "More Exact Modeling of COIL Laser Performance (Conference paper)," Proceedings of SPIE—The International Society for Optical Engineering , vol. 8429, 2012, Optical Modelling and Design II, Brussels, Belgium, Article No. 842928, Code 90944.

Pak A.O., et al., "Grid Receiver for Measuring of Laser Radiation Characteristics," Conference Proceedings, 11th International Conference on Laser and Fiber-Optical Networks Modeling, 2011, LFNM.

Sona A., "International Norms and EC Directives on Laser Safety in Medicine and Surgery", Proceedings of SPIE, The International Society for optical Engineering, 5610.1, 2004, pp. 60-64.

Wang Y.P., et al., "A Method for Evaluating High Energy Laser Beam Quality," Journal of Optoelectronics laser, 2001, vol. 12 (10), pp. 1029-1033.

Yang H., et al., "Evaluation of Beam Quality for High-Power Lasers," Proceedings of SPIE, 2007, vol. 6823, pp. 1-6.

\* cited by examiner

LASER BEAM CALIBRATION AND BEAM QUALITY MEASUREMENT IN LASER SURGERY SYSTEMS

CROSS-REFERENCE

This application is a divisional of and claims priority to U.S. patent application Ser. No. 15/299,745, filed Oct. 21, 2016, which claims the benefit under 35 U.S.C. § 119(e) of U.S. Provisional Patent Application No. 62/244,507, filed Oct. 21, 2015, the full disclosures of which are incorporated herein by reference.

FIELD OF THE INVENTION

Embodiments of the present invention relate to laser eye surgery systems, and more particularly, to laser beam calibration and laser beam quality measurement in laser surgical systems for eye surgery.

BACKGROUND OF THE INVENTION

Vision impairments such as myopia (near-sightedness), hyperopia (far-sightedness) and astigmatism can be corrected using eyeglasses or contact lenses. Alternatively, the cornea of the eye can be reshaped surgically to provide the needed optical correction. Eye surgery has become commonplace with some patients pursuing it as an elective procedure to avoid using contact lenses or glasses to correct refractive problems, and others pursuing it to correct adverse conditions such as cataracts.

With recent developments in laser technology, laser surgery is becoming the technique of choice for ophthalmic procedures. The reason eye surgeons prefer a surgical laser beam over manual tools like microkeratomes and forceps is that the laser beam can b e focused precisely on extremely small amounts of ocular tissue, thereby enhancing accuracy and reliability of the procedure. These in turn enable better wound healing and recovery following surgery.

Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm. Examples of laser systems that provide ultra-short pulsed laser beams include the Abbott Medical Optics iFS Advanced Femtosecond Laser, the IntraLase FS Laser, and the CATALYS Precision Laser System.

In laser systems for eye surgery, the quality of the laser beam is determined by how well the beam can be focused to a specific point, i.e., a circular area having a diameter typically of 1-2 microns, which is directly related to how well the beam can incise or ablate tissue. But, over time, the laser beam may fail to meet quality specifications due to optics misalignment, obscuration, or other failure modes. In this case, continued use of the laser system may result in cutting and ablation which is incomplete or degraded. Laser systems are therefore frequently tested to verify the beam quality. With many laser surgery systems, a beam quality test is performed every single day, well before the first patient is treated. A well-known beam quality test is performed by using the focused laser beam to make cuts in a test sample, such as a plastic sphere. The cuts are then inspected under magnification, and the beam quality is inferred from the characteristics of the cuts, such as the positions and the completeness of the cuts in the plastic sphere.

While this sample cutting technique may be relatively easily performed, it has several disadvantages. Initially, determining beam quality by inspecting cuts in a test sample is subjective and depends largely on the judgment of the inspector, typically an eye surgeon in a surgical facility, and not a laser system technician who may have better knowledge of the laser system. The sample cutting test is also an indirect qualitative measurement, rather than a direct quantitative measurement. In addition, no diagnostic information is provided when the inspector determines the system has failed the test. The sample cutting test also provides little or no information on changes in beam quality over time, which information may be useful in predicting an impending failure, or evaluating the cause of a failure.

Other techniques for measuring laser beam quality, such as the so-called bubble threshold test, have also been used, with varying degrees of success. But, these types of tests require more extensive equipment, time, and expertise. Thus, although these tests are useful in laboratory or factory settings, they are not well suited for daily use by an eye surgeon in a surgical facility. Consequently, engineering challenges remain in measuring laser beam quality in laser eye surgery systems.

In many laser eye surgery systems, the laser beam is directed via a scanning mirror. Position sensors associated with the scanning mirror can sense the position of the scanning mirror. If the laser eye surgery system is not properly calibrated, however, the actual position of the laser beam on or in the treatment volume of the eye may not correspond sufficiently precisely with the position information from the position sensors. As a result, engineering challenges also remain in designing improved techniques for calibrating laser eye surgery systems.

Therefore, there is a need for new and improved methods for measuring beam quality in laser eye surgery systems.

SUMMARY OF THE INVENTION

Hence, to obviate one or more problems due to limitations and disadvantages of the related art, this disclosure provides embodiments including methods and apparatus for measuring laser beam quality in a laser eye surgery system.

In a first aspect, methods for measuring beam quality in a laser eye surgery system provide a direct, quantitative quality measurement of the focused laser beam. The present methods may be automated or computer controlled, allowing them to be performed very quickly, and optionally, without the need of major test equipment or testing expertise.

In another aspect, a laser eye surgery system includes a computer which scans a focused laser beam over a reticle or target and determines beam quality via laser light reflected from the target. The target may have a grid pattern of lines, with the diameter of the focused laser beam determined based on a time interval for the scanned beam to move onto a line of the grid pattern.

In a further aspect, the beam in the laser eye surgery system may be calibrated using scanning mirror position information together with signals from laser light reflected from the target.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION OF THE DRAWINGS

Embodiments of this invention are generally directed to systems for laser-assisted eye surgery, and more particularly, to systems and methods for measuring and calibrating the beam quality in a laser eye surgery system.

Figure 1:
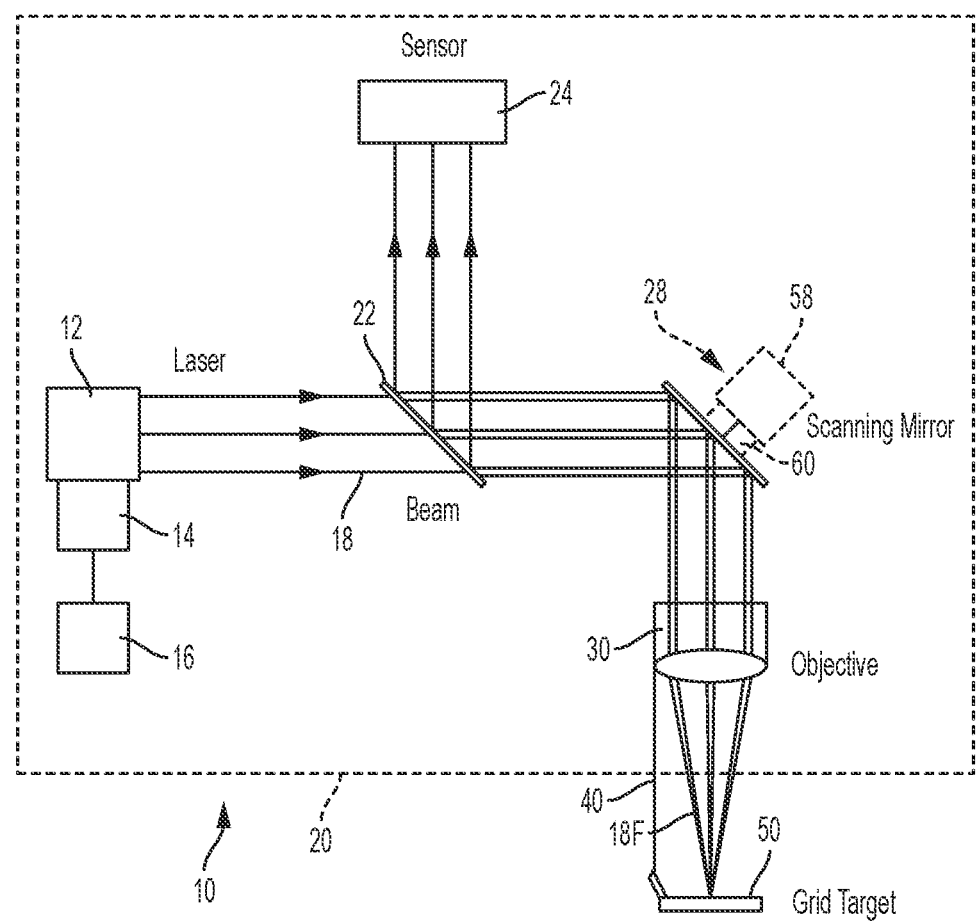
FIG. 1 is a schematic diagram of a laser eye surgery system.

As shown in FIG. 1, a laser eye surgery system 10 includes a laser assembly 12 which generates an unfocused laser beam 18. The laser assembly 12 and a display 16 are connected to a computer 14 which controls the operation of the laser assembly 12. The laser beam 18 projects out from the laser assembly 12, through the back side of a sensor mirror 22, and is reflected via a scanning mirror 28 to an objective lens 30, as described in detail for example in U.S. patent application Ser. No. 14/576,593, titled Confocal Laser Eye Surgery System, filed Dec. 19, 2014; U.S. patent application Ser. No. 14/666,743, titled Automated Calibration of Laser System and Tomography System with Fluorescent Imaging of Scan Pattern, filed Mar. 24, 2015; and U.S. patent application Ser. No. 14/191,095, titled Laser Eye Surgery System, filed Feb. 26, 2014, the full disclosures of which are incorporated herein by reference. A beamsplitter cube, or surface within a beamsplitter cube, or any other type of beam splitter with similar function, may be used in place of the sensor mirror 22.

In surgical use, the beam 18 is focused via the objective lens 30 and the focused beam 18F passes through a patient interface (such as a liquid filled suction cup on the eye) and into the eye where the focused laser beam cuts or ablates tissue. The laser assembly 12 may use a short pulse laser having a very short (e.g., approximately $10^{-13}$ to $10^{-9}$ seconds) pulse which delivers micro joules of energy in a small spot size of about 1.5 to 5 microns, providing various advantages over manual surgery, and over other lasers using longer pulses.

Figure 2:
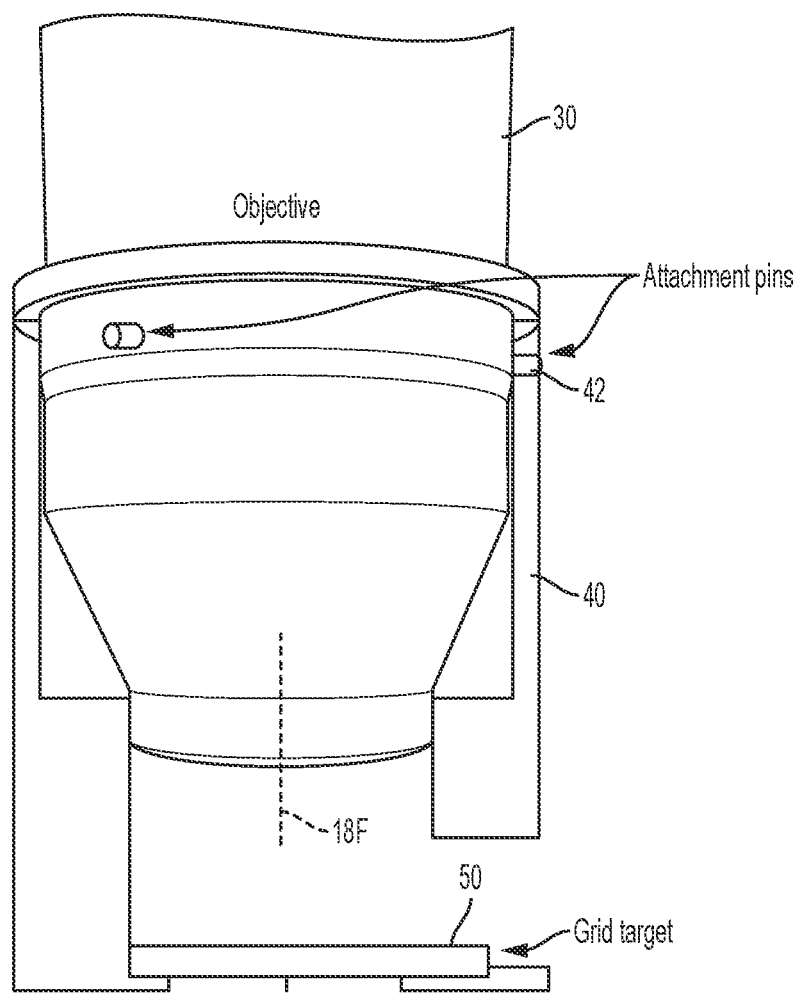
FIG. 2 is a side view of beam quality target supported on the objective lens of the system of FIG. 1.
Figure 3:
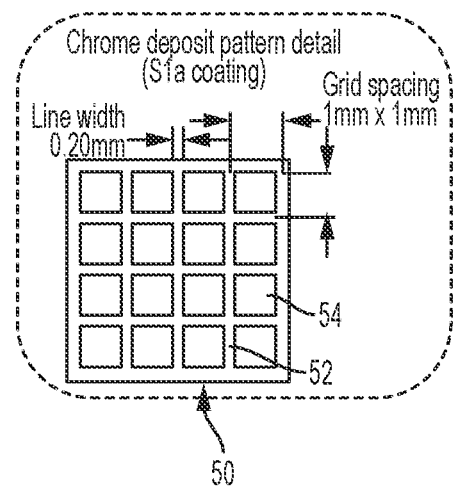
FIG. 3 is a plan view of the target shown in FIG. 2.

Referring now also to FIGS. 2 and 3, to measure beam quality a target 50 is supported at a precise position on a holder 40 and aligned with the objective lens 30. The target 50 has multiple lines 52 having high contrast with the background field 54 of the target. The holder 40 may be attached to the objective lens 30 via quick connect pins 42 or other fittings or fasteners ordinarily used to attach the patient interface. Alternatively, the holder 40 may be attached to the objective lens 30 using dedicated holder fittings, clamps or fasteners. In either case the target 50 is precisely located at a known position in three dimensions relative to the objective lens 30. The location of the target may also be precisely measured by a camera system integrated into the laser system instead of precisely locating the target by mechanical means. The laser assembly, computer, sensor mirror, sensor and scanning mirror may be entirely contained within an enclosure 20, with only a portion of the objective lens and the target outside of the enclosure.

When measuring beam quality, the focused laser beam 18F is scanned in a trajectory over the target 50. As the beam 18F crosses a line 52 on the target, a fraction of the laser light is reflected back to a sensor 24 via the objective lens 30, the scanning mirror 28 and the second side of the sensor mirror 22. To provide sufficient reflected or scattered laser light, the target 50 may have lines 52 of a reflective material such as chrome, aluminum, white ink, etc. on a transparent substrate such as glass, or on a non-reflective opaque substrate. The target may also be constructed so that the lines are transparent or non-reflecting or low-reflecting, and the background is reflective. The lines have precise straight edges. If the substrate is transparent, the sensor 24 may optionally be positioned below the target, i.e., with the target 50 between the objective lens 30 and sensor 24.

Referring to FIG. 3, the line width is advantageously several times greater than the beam diameter, so that the line completely reflects or blocks the beam as the beam crosses the line 52. In the example shown, the line width is 0.2 mm (100-200 times the nominal beam diameter) with 1 mm×1 mm grid spacing. A target having slits or non-reflective lines on a reflective background may also be used. The beam diameter as used here means the width or dimension of the beam in a particular direction of scan, and not necessarily strict circular symmetry.

The target 50 at a location at a fixed distance from the objective lens 30 only fully characterizes the beam at that location, allowing for evaluation of a two dimensional plane. To evaluate the beam in three dimensions, the target 50 may be placed at various distances from the objective lens. For example, two or more targets 50 may be placed at different vertical positions relative to the objective lens 30, with beam quality measured with the beam focused initially on the first target and then on the second target. The target may optionally be provided in an optical element, such as a prism that may be temporarily move into the beam path to measure beam quality and then returned to a storage position not in the beam path. The target 50 may also be on a stage which is movable in the Z-axis. In this case, by comparing measurements made at different Z-axis dimensions, the position of the focal plane (where the beam is best focused) may be identified.

The scanning mirror 28 may include a Z-scan device 58 and an XY-scan device 60. The Z-scan device 58 may be used to vary a convergence/divergence angle of the beam 18 and thereby change a location of the focal point in the Z direction, i.e., the direction of propagation of the beam 28, for example by using movable lenses. Alternatively, the objective lens 30 is moved in the Z-direction to focus the beam in the Z direction via an actuator such as a voice coil. The XY-scan device 60 deflects the beam 28 in the X and Y dimensions transverse to the Z direction by deflecting one or more mirrors.

Some laser eye surgery systems include a sensor 24 as part of a confocal detection assembly. In these systems, laser light reflected from the eye during surgery is detected by the confocal detection assembly to generate a reflected light intensity signal. This signal is coupled with beam scanning position information and processed in a computer to image or locate structures of the eye. Consequently, in systems having a sensor 24 included in a confocal detection assembly, during beam quality measuring, the sensor of the confocal detection assembly may be used to generate an intensity signal indicative of the intensity of the sensed laser light reflected from the target, rather than from the eye. In this case, no separate additional sensor is needed.

The quality of the focused beam 18F, i.e., the minimum focused beam size, may be measured by scanning the beam over the target 50, with the target positioned relative to the objective lens 30 so that the grid lines 52 are in the plane of focus. Laser light reflected by the grid lines 52 is detected and analyzed, providing a measurement of the cross section of the beam 18F. As the beam 18F moves across a grid line 52, the detected signal corresponding to the reflected laser light will show a very steep rise if the beam 18F is well focused. Although beam shape is also an aspect of beam quality, changes in beam shape will also change the measured beam width in one direction or another. Measuring the beam width in one or two directions will reveal the beam quality in virtually all practical cases.

The measurement process may be performed via the following steps:

1. Determining a Trajectory

Determine a trajectory for scanning the laser beam over the target. The parameters used in calculating the trajectory include the grid line positions, the angle of the beam scan across the lines, and the length of the scan across each line. The scan trajectory of the beam 18F may be selected so that the beam crosses a grid line 52 in two orthogonal directions. This trajectory results in the short pulse signals. As short pulse signals may be more challenging to resolve, longer pulse signals may be generated by scanning the beam at a low angle (e.g., 5-30 degrees) to the grid line, allowing for higher resolution of the signals via the sensor 24 and the computer 14.

In a basic form, the scan trajectory may be a raster style scan starting at one corner of the target and scanning from in sequential or alternating horizontal rows down to the opposite corner of the target, followed by vertical scanning of columns. Many other types of trajectories, including circular, spiral, and interrupted or segmented trajectories, may be used. Of course, since the scan angle (the angle at which the beam scans over the line) is a factor in measuring beam quality, orthogonal straight line trajectories may be easiest to use.

2. Scanning the Focused Beam

Scan the focused beam in the selected trajectory over the target via movement of the scanning mirror 28 in two dimensions. The sensor 24 senses the reflected or scattered laser light and provides a corresponding output signal to the computer 14. The computer 14 or other circuitry converts the sensor output signal into a digital signal which is stored and analyzed by the computer 14. The beam 18F is aimed via the mirror 28 over a range of X-axis and Y-axis movement. The beam is typically moved in incremental steps. With a step size of e.g., 1 micron, and a beam diameter of 1.5 microns, the detected signal changes from zero to a maximum in 1-2 steps. In the example shown, a full range of X or Y axis movement over e.g. 25 mm may be 150 steps.

Laser eye surgery systems 10 are generally designed to perform surgery within a volume or space of the eye, known as the treatment volume, which in a selected focal plane or Z-axis dimension, is approximately the diameter of an adult human cornea, usually about 16 mm. The beam 18F may be used to perform surgery at all positions within the treatment volume. Consequently, it is desirable to be able to measure beam quality at all positions within the treatment volume. By moving the beam in a trajectory across an e.g., 22-28 mm square grid, as shown in FIG. 3, beam quality can be measured at all positions within the treatment volume in most or all laser eye surgery systems.

As the beam 18F moves away from the center position, beam quality tends to degrade (i.e., beam diameter increases or becomes elliptical or asymmetric) due to the characteristics of the optical components used to aim and focus the beam. Consequently, an accurate assessment of beam quality involves measuring the beam diameter at all positions within the treatment volume.

3. Generating a Table

For each line crossing or coordinate, generate a table of sensor output versus beam position. The computer 14 is also connected to the scanning mirror 28 with the scan mirror angle instantaneously provided to the computer 14. The computer determines the beam position on the target 50 based on the scan mirror angle. The beam scanning velocity is known as it is a function of the movement of the scanning mirror 28. The sensor output is the digitized signal from the sensor, which is a function of sensed reflected light.

4. Determining Beam Width

For each line crossing, determine the beam diameter from the data table created in step 3 above. A variety of algorithms can be used. The algorithm may measure the time interval between 10% and 90% of the maximum signal to calculate the beam diameter. The time interval for a high quality tightly focused beam having a small diameter is less than time interval for a lower quality less focused beam having a larger diameter. Based on the digitized data from the sensor 24, the computer 14 calculates an average or representative slope of the signal. The slope and beam scanning velocity is proportional to the beam diameter. Specifically, since the beam scanning velocity is known, and the slope is a function of the time interval between the leading and trailing edges of the beam intersecting the line, the diameter of the beam may be calculated. The computer may then display a number indicative of the beam diameter on the display 16. If the number is within the system specification, the system passes. If not, the system fails. In this case, the computer may optionally lock out the system from further use until the system is brought into specification, typically adjusting alignment or other parameters of optical components of the system.

This process described above in steps 1-4 can be repeated as the focus of the laser beam is adjusted in steps, so that the beam width can be calculated as a function of focus position. The best focus position is determined from this analysis by interpolating the data to find the minimum beam width position.

As used here, the term line or grid line includes slits. Velocity means a speed and a direction relative to a grid line 52. Intersect means directing the beam over or onto a line or other target feature sufficiently to generate the signals used for performing the calibration and measurement methods described. Although FIG. 3 shows continuous lines, line segments may also be used. Targets having curved lines, such as rings or spirals may optionally b e used with correspondingly scanning trajectories.

A method for determining quality of a focused laser beam in a laser eye surgery system may be performed by scanning the focused laser beam in a trajectory over a target having two or more lines, and determining the position of the focused laser beam on the target during the scanning. Laser light reflected or scattered by one of the lines as the laser crosses the line is sensed and digitized. A table of digitized sensed laser light values versus position of the beam is then generated, and the diameter of the focused laser beam is determined based on the table. In this method the target may have a grid of perpendicular lines, with each line having a width at least 5 times greater than a diameter of the focused laser beam.

In addition to the methods described above for measuring beam quality, and beam quality within a treatment volume, since measurements are made by sensing the beam passing over lines of a known geometry in the treatment volume, methods for simultaneously calibrating the scanned beam (or verifying the calibration of the scanned beam) may also be performed, while measuring the beam quality. Consequently, the methods are useful for both verifying targeting and beam quality within the treatment volume. Since the target can be viewed by an on-board imaging system (camera, in 2D), the calibration of position and beam quality may also b e mapped to the camera image, thus calibrating the targeting displayed to the surgeon operating the system.

Calibration may be performed by scanning a focused laser beam in a trajectory over the target via a scanning mirror, and sensing laser light reflected or scattered by a first line of the target at time T1 when the laser beam intersects a first edge of the first line to determine an actual laser beam position. The first edge can be a leading edge or a trailing edge of the first line of the target. The position of the scanning mirror is also sensed at time T1, for example via feedback position sensors on the scanning mirror. These steps are repeated with the laser beam intersecting subsequent lines at subsequent times. A table of digitized actual laser beam position values versus sensed scanning mirror position values can then be generated, with the calibration of the achieved based on the table.

During the calibration and/or beam quality measurement procedures the target may be precisely fixed in a known or centered position relative to the objective lens, so that actual beam positions on the target can be calibrated back to scanning mirror positions. Alternatively, if the target is not precisely centered relative to the objective lens, pixels on a display may be mapped to actual locations on the target, and an offset function used to compensate for an off center position of the target.

All patents and patent applications cited herein are hereby incorporated by reference in their entirety.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can b e performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

The invention claimed is:

1. A method for calibrating a laser eye surgery system, comprising:
   a. scanning a focused laser beam in a trajectory over a target via a scanning mirror, the target having a plurality of lines;
   b. sensing laser light reflected or scattered by a first line of the target at time T1 when the laser beam intersects a first edge of the first line to determine an actual laser beam position;
   c. sensing a position of the scanning mirror at time T1;
   d. repeating steps A-C, the laser beam intersecting subsequent lines at subsequent times;
   e. generating a table of digitized actual laser beam position values versus sensed scanning mirror position values at time T1 and the subsequent times; and
   f. calibrating the laser eye surgery system based at least in part on the table generated in step E.

2. The method of claim 1 further including mapping pixels on a display of the system to positions on the target.

3. The method of claim 1, wherein the laser beam is focused via an objective lens and further including supporting the target on a holder attached to the objective lens.

4. The method of claim 1 wherein the focused laser beam is an infrared femtosecond laser beam, a visible light laser beam, or an ultraviolet laser beam.

5. A laser eye surgical system, comprising:
   a laser assembly for generating a laser beam;
   a sensor mirror between the laser assembly and a scanning mirror;
   a sensor positioned to detect light reflected by the sensor mirror;
   an objective lens between the scanning mirror and a target;
   a target holder configured to support the target at a plurality of different distances from the objective lens along a propagation direction of the laser beam; and
   a computer linked to the laser assembly, the sensor, the scanning mirror and the target holder;
   wherein the laser assembly projects the laser beam through the sensor mirror to a scanning mirror, wherein the laser beam is reflected by the scanning mirror and projected through the objective lens and onto the target;
   wherein the target has a plurality of lines reflecting laser light of the laser beam to the sensor via the objective lens, the scanning mirror and the sensor mirror, and the sensor provides a signal to the computer based on sensed light reflected from the target;

wherein the computer is configured to control the target holder to successively support the target at the plurality of different distances from the objective lens, to receive a plurality of signals from the sensor while the target is successively supported at the plurality of different distances from the objective lens, and to compare the received plurality of signals to identify a focal plane position along the propagation direction of the laser beam where the laser beam is best focused.

6. The system of claim 5, wherein the target comprises a grid of perpendicular lines.

7. The system of claim 6, wherein the target comprises reflective metal lines on a transparent substrate.

8. The system of claim 5, wherein the objective lens has patient interface attachment fittings, and wherein the target is on a holder attached onto the objective lens via the patient interface attachment fittings.

9. The system of claim 5, wherein the computer, the laser assembly, the sensor mirror, the sensor, and the scanning mirror are within an enclosure, and wherein the target and a portion of the objective lens are outside of the enclosure.

10. The system of claim 9, wherein the laser assembly, the sensor mirror and the sensor are in fixed positions within the enclosure.

11. The system of claim 5, wherein the laser beam has a diameter of 1-2 microns and wherein the target has lines at least 40 times wider than the beam diameter.

* * * * *